US006759654B1

United States Patent
Mankos et al.

(10) Patent No.: US 6,759,654 B1
(45) Date of Patent: Jul. 6, 2004

(54) HIGH CONTRAST INSPECTION AND REVIEW OF MAGNETIC MEDIA AND HEADS

(75) Inventors: Marian Mankos, San Francisco, CA (US); David A. Soltz, San Jose, CA (US); Harald F. Hess, La Jolla, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/345,696

(22) Filed: Jan. 16, 2003

Related U.S. Application Data

(60) Provisional application No. 60/438,649, filed on Jan. 7, 2003.

(51) Int. Cl.[7] .......................... G01N 23/225; G11B 9/10
(52) U.S. Cl. ........................................ 250/307; 250/310
(58) Field of Search .................................. 250/307, 310

(56) References Cited

U.S. PATENT DOCUMENTS

2003/0127593 A1 * 7/2003 Shinada et al. ............. 250/310

* cited by examiner

Primary Examiner—John R. Lee
Assistant Examiner—James Leybourne
(74) Attorney, Agent, or Firm—Okamoto & Benedicto LLP

(57) ABSTRACT

One embodiment disclosed relates to a method for inspecting or reviewing a magnetized specimen using an automated inspection apparatus. The method includes generating a beam of incident electrons using an electron source, biasing the specimen with respect to the electron source such that the incident electrons decelerate as a surface of the specimen is approached, and illuminating a portion of the specimen at a tilt with the beam of incident electrons. The specimen is moved under the incident beam of electrons using a movable stage of the inspection apparatus. Scattered electrons are detected to form image data of the specimen showing distinct contrast between regions of different magnetization. The movement of the specimen under the beam of incident electrons may be continuous, and data for multiple image pixels may be acquired in parallel using a time delay integrating detector.

22 Claims, 6 Drawing Sheets

100

HIGH CONTRAST INSPECTION AND REVIEW OF MAGNETIC MEDIA AND HEADS

This application claims the benefit of U.S. provisional patent application No. 60/438,649, filed Jan. 7, 2003, by inventors Marian Mankos, David A. Soliz, and Harald F. Hess, entitled "High Speed Inspection and Review of Magnetic Media and Heads."

BACKGROUND OF THE INVENTION

1. Field of the Invention

The present invention relates generally to magnetic specimens. More particularly, the present invention relates to examining or inspecting magnetic materials or devices.

2. Description of the Background Art

In recent years, the areal density of disk drives has increased by about 60% to 100% per year. This exponential increase is comparable to the increase in density of integrated circuit chips as described by Moore's law (predicting that the density of IC chips doubles about every 18 months). The areal density increases have been achieved by developing new materials for magnetic media and improving read/write heads.

As the technology of magnetic media and heads continue to advance, it is desirable to develop and improve techniques for inspecting or reviewing the magnetic media and/or heads. Conventional techniques for examining magnetic specimens include Lorentz microscopy and magnetic force microscopy.

Lorentz microscopy involves transmission of high energy electrons through thin samples of magnetic specimens. The magnetic contrast occurs due to the interaction of the electrons passing through the magnetic induction due to the magnetization of the specimen. Components of the magnetic induction normal to the electron beam cause deflection of the beam. A significant disadvantage of Lorentz microscopy is that it is applied to specimens thin enough for electron transmission. This typically requires substantial sample preparation that is often destructive of the specimen being examined.

Magnetic force microscopy (MFM) is a standard technique for investigating magnetic media. MFM uses a magnetic tip on a small cantilever to probe a magnetic field above a surface of a specimen. The magnetic field causes a force that deflects the cantilever. MFM does not require preparation of an electron thin sample. However, MFM has various limitations. In particular, MFM requires the entire area of interest to be scanned or translated under the to magnetic tip. Hence, examining a relatively large area using MFM is a relatively slow process.

Another conventional technique for examining magnetic media involves writing and reading the media on a spin stand with a magnetic reader head. Such a technique is often used to screen heads and to characterize media. A further application is to recover lost data from hard disks by just reading the data with a flying head. For data recovery to succeed using the conventional technique the head must fly very low (of order 5–30 nm) over the spinning disk. This puts stringent demands on the flatness and perfection of the disk surface, for this method to be viable. For this reason a crashed or otherwise damaged disk is often not be recoverable in a disk drive or with a spin stand approach. An additional data recovery limitation is that the resolution is limited to that of the read head and one cannot image partially erased track fragments.

SUMMARY

Figure 1:
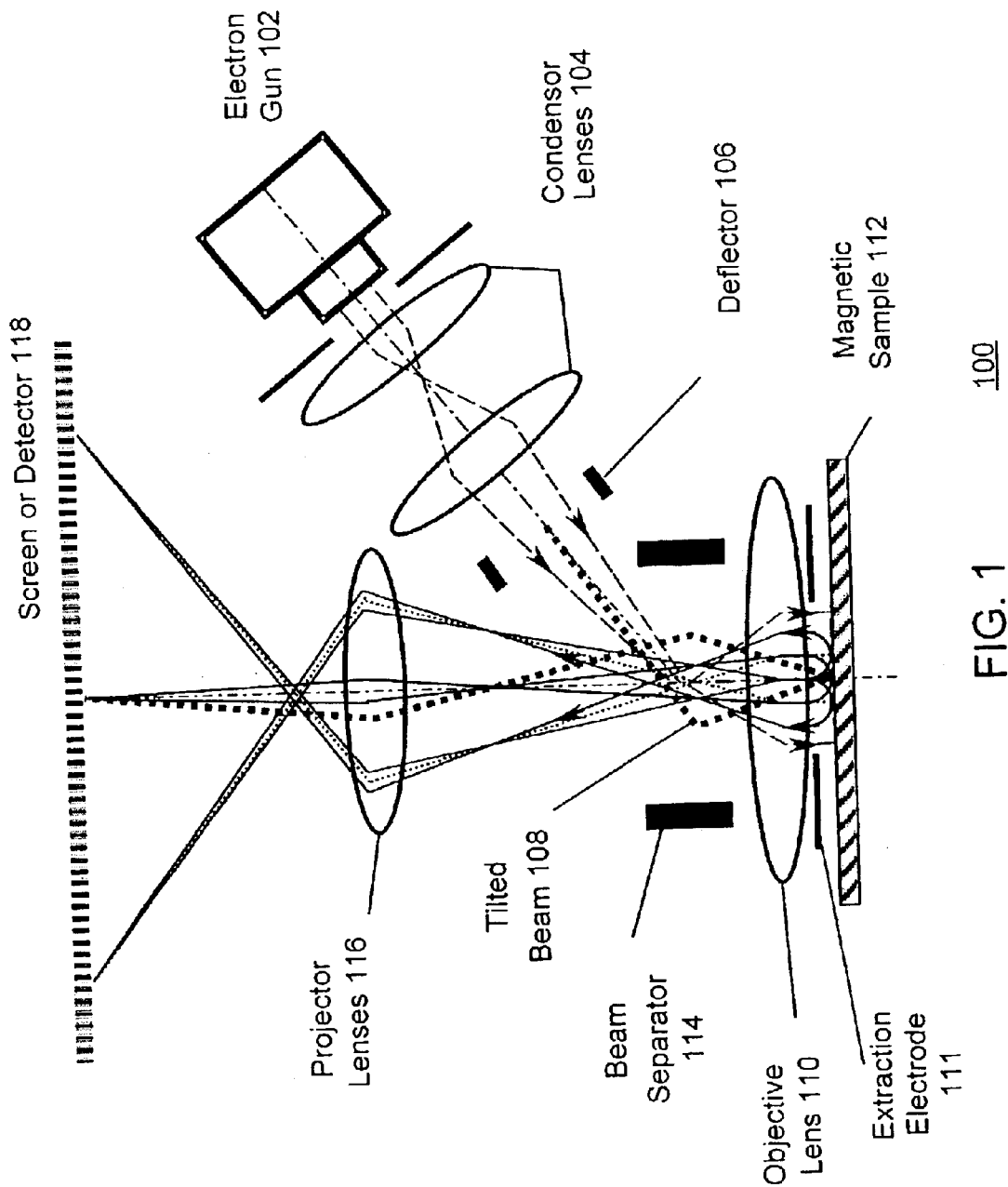
FIG. 1 depicts an apparatus for inspection or review of a magnetized specimen in accordance with an embodiment of the invention.

One embodiment of the invention pertains to a method for inspecting or reviewing a magnetized specimen using an automated inspection apparatus. The method includes generating a beam of incident electrons using an electron source, biasing the specimen with respect to the electron source such that the incident electrons decelerate as a surface of the specimen is approached, and illuminating a portion of the specimen at a tilt with the beam of incident electrons. The specimen is moved under the incident beam of electrons using a movable stage of the inspection apparatus. Scattered electrons are detected to form image data of the specimen showing distinct contrast between regions of different magnetization. The movement of the specimen under the beam of incident electrons may be continuous, and data for multiple image pixels may be acquired in parallel using a time delay integrating detector.

Another embodiment relates to a method for recovering data from a magnetic storage medium. The method includes generating a beam of incident electrons using an electron source, biasing the medium with respect to the electron source such that the incident electrons decelerate as a surface of the medium is approached, and illuminating a portion of the medium at a tilt with the beam of incident electrons. Scattered electrons are detected to form image data of the specimen showing distinct contrast between regions of different magnetization. Finally, binary data is extracted from the image data. The binary data may be decoded to recover data previously stored on the magnetic storage medium.

Another embodiment relates to an automated inspection apparatus configured to inspect arrays of magnetic read/write heads. The apparatus includes an electron source for generating a beam of incident electrons, and a bias circuit for biasing the array of heads with respect to the electron source such that the incident electrons decelerate as a surface of the array of heads is approached. Electron optics is used to illuminate the array of heads at a tilt with the beam of incident electrons. A movable stage is used for moving the array of heads under the beam of incident electrons. Finally, a detector detects scattered electrons to form image data of the array of heads showing contrast between regions of different magnetization. The movable stage may be moved continuously under the beam of incident electrons, and the detector may comprise a time delay integrating detector which is a type of parallel detector.

Another embodiment relates to an apparatus configured to examine a magnetic storage medium. The apparatus includes an electron source for generating a beam of incident electrons and a bias circuit means for biasing the medium with respect to the electron source such that the incident electrons decelerate as a surface of the medium is approached. The apparatus also includes electron optics for illuminating the medium at a tilt with the beam of incident electrons. A detector for detecting scattered electrons is used to form image data of the medium showing contrast between regions of different magnetization. Finally, an image processor for extracting binary data from the image data. A data decoder may be utilized to decode the binary data to recover data previously stored on the magnetic storage medium.

DETAILED DESCRIPTION

FIG. 1. depicts an apparatus 100 for inspection or review of a magnetized specimen in accordance with an embodiment of the invention. The apparatus 100 is a type of low energy electron microscope. The apparatus 100 as depicted includes an electron gun or source 102, condensor lenses 104, a deflector 106, an objective lens 110 which includes an extraction electrode 111, a magnetic sample or specimen 112, a beam separator 114, a projector lens 116, and a screen or detector 118. While certain components are illustrated in FIG. 1 for purposes of discussion, alternate embodiments of an electron beam apparatus in accordance with the invention may include other components varying from or adding to those illustrated.

The electron gun 102 is a source of electrons for the incident beam. The electron gun 102 may comprise, for example, a thermionic electron gun, a field emission gun, or another type of source. The condenser lenses 104 focuses the electrons from the gun 102 into a beam. The condensor lenses may comprise, for example, magnetic lenses.

The deflector 106 may be used to shift or adjust the direction of the beam of incident electrons. The deflector 106 may be implemented using a magnetic deflector, an electrostatic deflector, or using a combined electrostatic-magnetic deflector. In accordance with an embodiment of the invention, the deflector 106 may be utilized to adjust a tilt angle of the beam of incident electrons as it impinges upon the magnetic specimen 112. The tiled beam 108 after deflection is illustrated in FIG. 1. As illustrated, the beam 108 impinges upon the magnetic specimen 112 at an angle with respect to the normal from the surface of the specimen 112.

The tilted electron beam 108 is focused onto the magnetic specimen 112 by the objective lens 110. The specimen may be set on a specimen holder (not illustrated). A bias circuit applies a voltage bias to the specimen. For low energy electron microscopy, the bias may be a few hundred volts or less with respect to the source or cathode. When the specimen is biased at the proper potential with respect to the cathode, the electrons are reflected and scattered above the surface. This type of imaging mode may be referred to as mirror electron microscopy, and the potential at which the electrons are reflected just at the surface of the sample is referred to as the mirror potential. The value of the mirror potential depends on the angle of tilt of the beam with respect the sample, but it typically occurs at a value from near zero to a few tens of volts positive of the electron source. The scattered electrons leaving the sample 112 are focused by the objective lens 110 to form an image of the specimen surface.

A beam separator 114 is utilized to separate apart the scattered electron beam (the beam coming from the magnetized specimen 112) from the primary electron beam (the beam coming from the gun 102). In one embodiment, the beam separator 114 may comprise a Wien filter that separates the two beams based on their velocities. Alternatively, the beam separator 114 may comprise bending magnets configured to separate the beams. The projector lens 116 images the beam onto the screen or detector 118. The image formed on the screen or detector 118 is that of the magnetized specimen 112.

The image data may be viewed by a user and/or is electronically processed and analyzed by the inspection or review system. If the magnetic specimen 112 comprises a magnetic medium, then binary data may be extracted from the image data, where the binary data represents information stored on the magnetic medium. This extraction may be performed by using an image processing system. If the specimen 112 comprises magnetic read/write heads, then the image data may be processed to detect faulty heads. Such inspection may be advantageously performed prior to dicing and individual testing of the heads.

In accordance with one particular embodiment, the magnetic specimen 112 may be moved continuously under the e-beam by a movable stage during an inspection process. This advantageously speeds up the process of inspection. Such an inspection system may utilize a time delay integrating (TDI) electron detector as the detector 118. The operation of an analogous TDI optical detector is disclosed in U.S. Pat. No. 4,877,326, entitled "Method and Apparatus for Optical Inspection of Substrates," inventors Chadwick et al., and assigned at issuance to KLA Instruments Corporation. The disclosure of U.S. Pat. No. 4,877,326 is hereby incorporated herein by reference. The image information may be processed directly from a 'back thin' TDI electron detector, or the electron beam may be converted into a light beam and detected with an optional optical system and a TDI optical detector. As one alternative to using a TDI electron detector, such an inspection system may utilize a camera type detector.

The apparatus 100 may be configured to have a large incident beam current and a large field size. Such a configuration would advantageously provide for high throughput inspection processes. In addition, a second electron beam (not shown in FIG. 1) may be advantageously incorporated to maintain charge control at the surface of the specimen 112. The use of such a second electron beam is described in further detail in U.S. patent application Ser. No. 09/854,332, entitled "Apparatus for Inspection of Semiconductor Wafers and Masks Using a Low Energy Electron Microscope with Two Illuminating Beams," inventors Lee Veneklasen, David L. Adler and Matthew Marcus, filed May 11, 2001. The aforementioned patent application is hereby incorporated by reference in its entirety.

Figure 2:
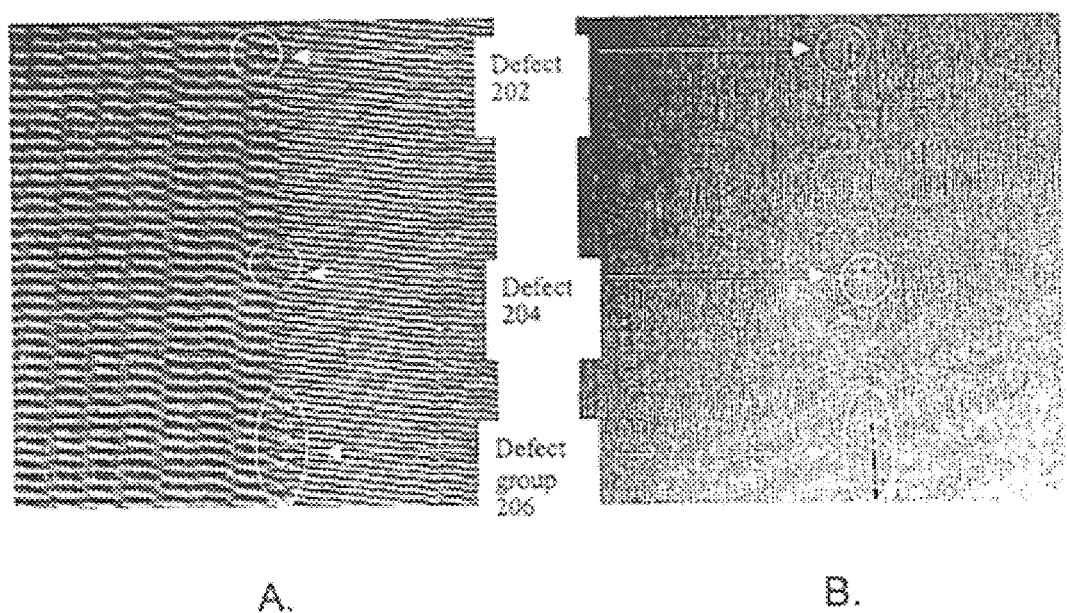
FIG. 2 depicts results of the technique for inspection or review of a magnetized specimen in accordance with an embodiment of the invention.

FIG. 2 depicts results of the technique for inspection or review of a magnetized specimen in accordance with an embodiment of the invention. The field of view is 80 micrometers wide in both images A and B.

The first image A on the left was obtained experimentally using a tilted incident beam and shows predominantly magnetic contrast. The bias on the specimen and focusing by the objective lens were adjusted to obtain the contrast shown. The horizontal lines represent magnetic bits recorded onto the hard disk prior to the experimental viewing. Larger period bits are spaced approximately 3 micrometers apart and are shown on the left side of the first image A. Smaller period bits are spaced approximately 1.8 micrometers apart and are shown on the right side of the image A.

The second image B on the right shows the same area of the same specimen as shown in the first image A, but it was obtained experimentally using a beam normal to the surface. The second image B shows predominantly topographical contrast.

Individual magnetic defects (202 and 204) and a group of magnetic defects 206 are present in the imaged area. The defects (202, 204, and 206) appear to be somewhat visible in the topological image B, but the topological image B neither clearly shows the defects, nor shows whether the defects are magnetic or non-magnetic in nature. The magnetic image A more clearly reveals the defects with its high contrast image data and further indicates the magnetic nature of the defects, differentiating them from non-magnetic defects. Thus, magnetic and surface topology features may be advantageously correlated by analyzing both the tilted image A and the non-tilted image B.

The distinct contrast in the magnetic image A advantageously enables the magnetic specimen, whether magnetic media or read/write heads, to be inspected with a high throughput inspection apparatus. Furthermore, the magnetic image A shows the high spatial resolution obtainable with this technique. Such high spatial resolution may advantageously be used to examine defects in greater detail or to reveal defects otherwise overlooked with other examination techniques.

Figure 3:
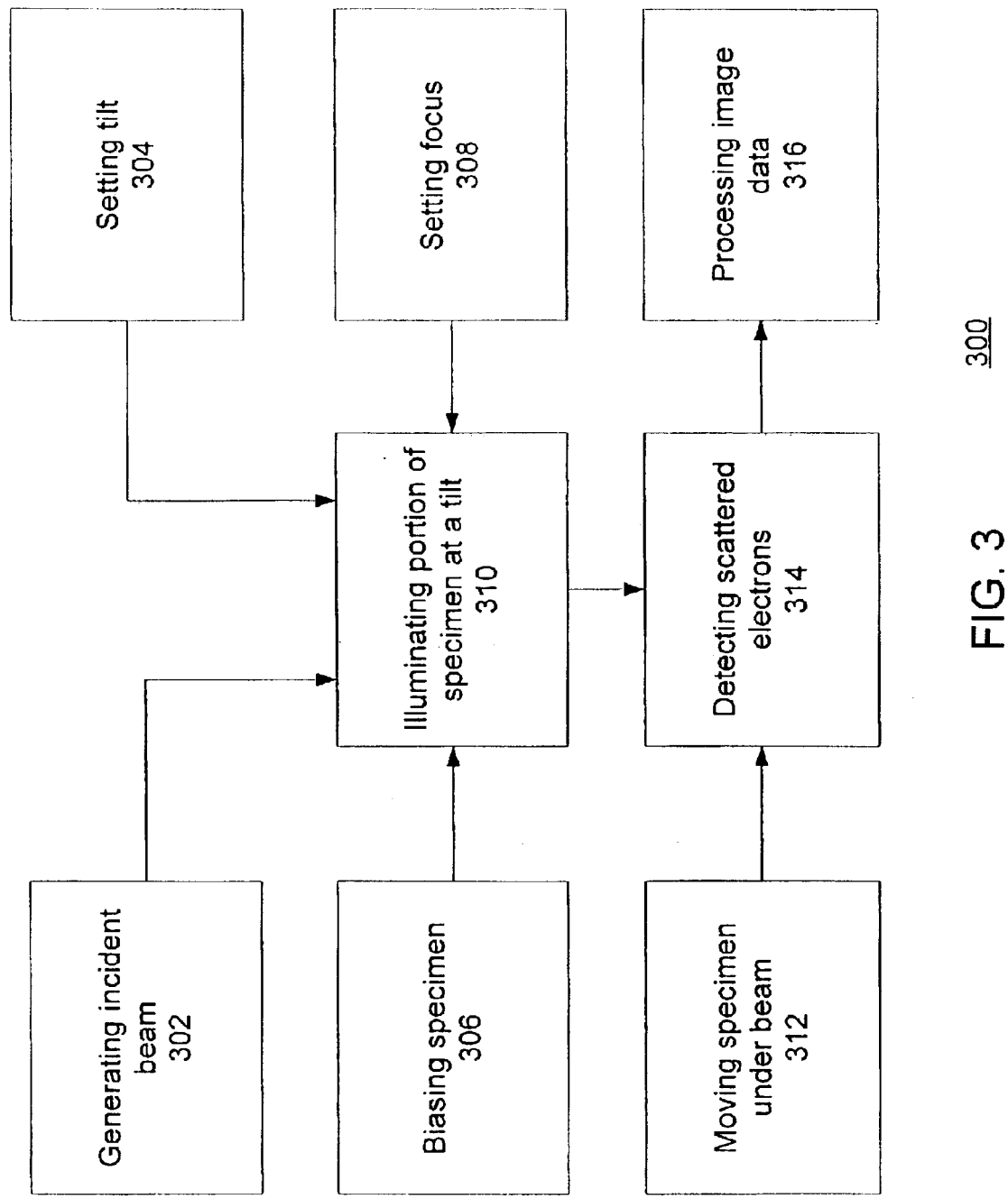
FIG. 3 is a flow chart showing a method for inspection or review of a magnetized specimen in accordance with an embodiment of the invention.

FIG. 3 is a flow chart showing a method 300 for inspection or review of a magnetized specimen in accordance with an embodiment of the invention. A beam of incident electrons is generated 302 using an electron source 102. The beam is tilted 306 such that it is incident at an angle to the normal of the surface of the specimen. The tilting may be done, for example, by using a beam deflector 106.

The magnetic specimen is biased 306 with respect to the electron source such that the incident electrons decelerate as a surface of the specimen is approached. In one embodiment, the specimen is biased slightly negative with respect to the mirror potential such that incident electrons are primarily reflected above a surface of the specimen. The mirror potential is the potential at which electrons are reflected from the surface of the sample. The mirror potential varies depending on the tilt of the beam, but it is typically between near zero and a few tens of volts positive with respect to the electron source. In another embodiment, the specimen is biased at or slightly positive to the mirror potential such that the incident electrons are primarily reflected at or near a surface of the specimen. In the former case, the applicants believe that image data obtained has contrast primarily due to magnetic characteristics. In the latter case, the applicants believe that the image data obtained includes both magnetic and topological information.

In addition, the focus is set 308 to an appropriate level by adjusting the strength of the objective lens. In one embodiment, the image may be defocused from the surface of the specimen such that an area above the surface is in focus.

With the tilt, bias, and focus parameters set as described above, the specimen is illuminated 310 with the tilted beam of incident electrons. In one embodiment, a relatively wide field of view is illuminated 310 in order to enable parallel imaging of multiple pixels and achieve high throughput inspection of the specimens.

Scattered electrons are detected 314 to form image data of the specimen showing contrast between regions of different magnetization. In one particular embodiment, the specimen is moved 312 continuously under the beam. In accordance with such an embodiment, a time delay integrating detector may be advantageously utilized, for example.

The image data may be processed 316 using an image processing system. The processing may, for example, extract binary data from the image data, where the binary data represents information stored on the magnetic medium. As another example, the processing may be used to inspect read/write heads to detect faulty heads. This enables inspecting several hundred heads at once while they are still attached together in a bar after fabrication and prior to dicing. This advantageously may be used to avoid the slow and expensive process of mounting and individual testing of each head.

Figure 4:
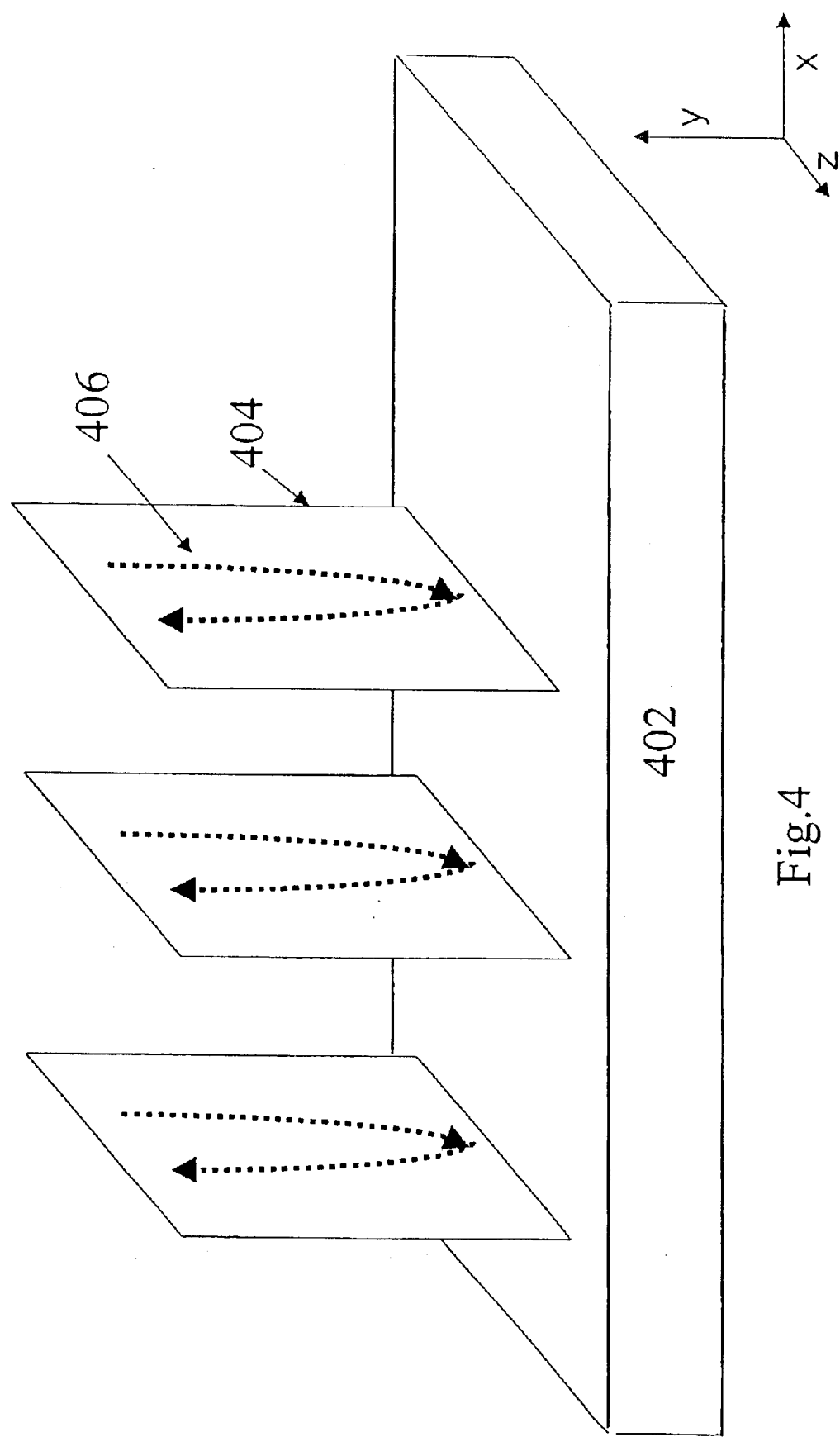
FIG. 4 is a schematic illustrating the parabolic trajectory of electrons reflecting off of the electric field of a nonmagnetic sample when there is a finite incoming angle or tilt in the incident electrons.

FIG. 4 is a schematic illustration depicting the path of the electrons as they reflect off the surface 402. The electron trajectory 406 forms a parabola in the yz plane 404 when either the sample or initial electron direction is tilted in the yz plane. This represents the case when there is no magnetic field emanating from the sample surface 402.

Figure 5:
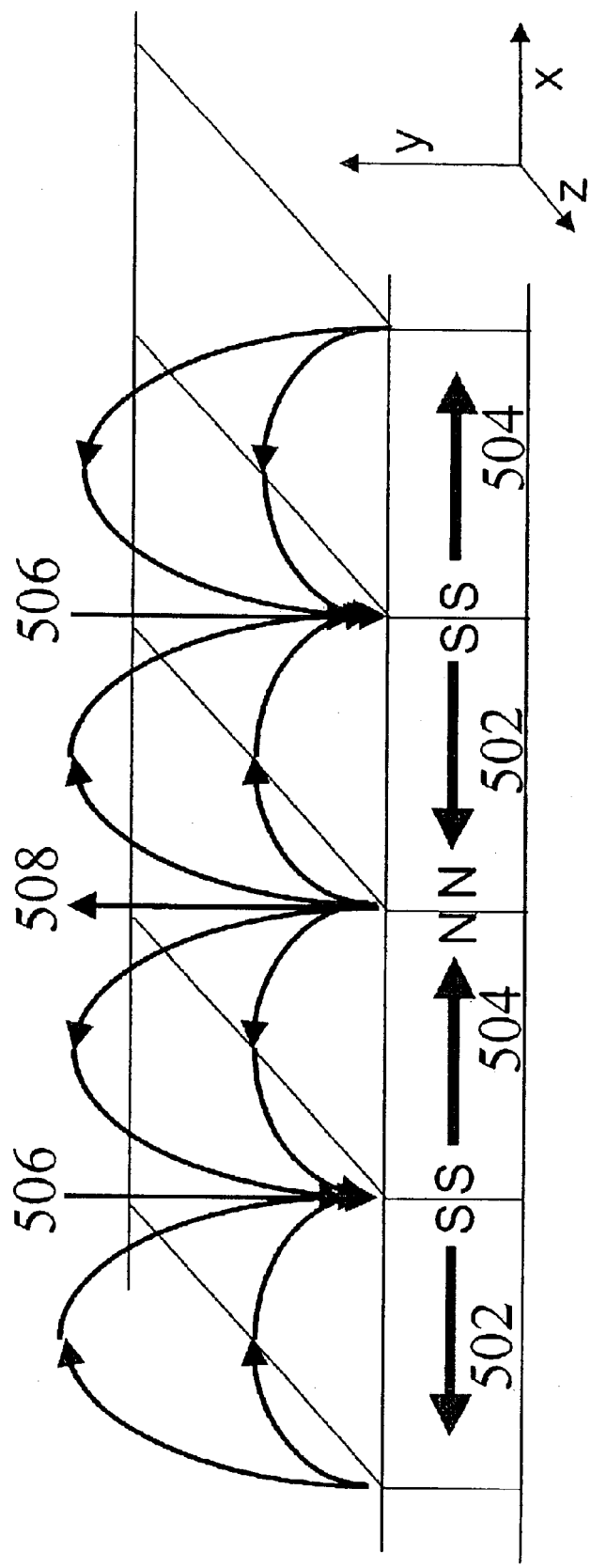
FIG. 5 is a schematic illustration depicting the surface of a magnetized specimen and associated magnetic field lines.

FIG. 5 is a schematic illustration depicting the surface of a magnetized specimen and associated magnetic field lines. As shown in the drawing, the surface of the magnetized specimen includes magnetic bits with the magnetization (dipole) direction lo the left 502 and magnetic bits with the magnetization (dipole) direction to the right 504. Such domains may be present, for example, on a magnetic medium on which data has been written. Above the surface, magnetic field lines or flux are illustrated that are associated with and caused by the magnetic bits (502 and 504). Note that above the transitions or borders between the domains, the field lines are either flowing downward 506 or upward 508. The downward flowing field lines 506 are present above a border that is between magnetic bits whose magnetization directions are pointed outward or away from the border. The upward flowing field lines 508 are present above a border that is between magnetic bits whose magnetization directions are pointed inward or towards the border.

Electron trajectories are influenced by such magnetic field lines in accordance with the Lorentz force equation of physics. According to the Lorentz force equation, electron trajectories are not influenced by components of field lines that are parallel to the trajectories; they are only influenced by components of field lines that are perpendicular to the trajectories. In other words, only components of the magnetic field lines that are normal to an electron trajectory give rise to a deflection of the trajectory.

In this case, applicants believe that the electrons from the untilted beam are not substantially influenced by the downwardly flowing or upwardly flowing field lines near the borders between magnetic bits. As such, applicants believe that high magnetic contrast is problematic to obtain with an untilted incident beam.

Figure 6:
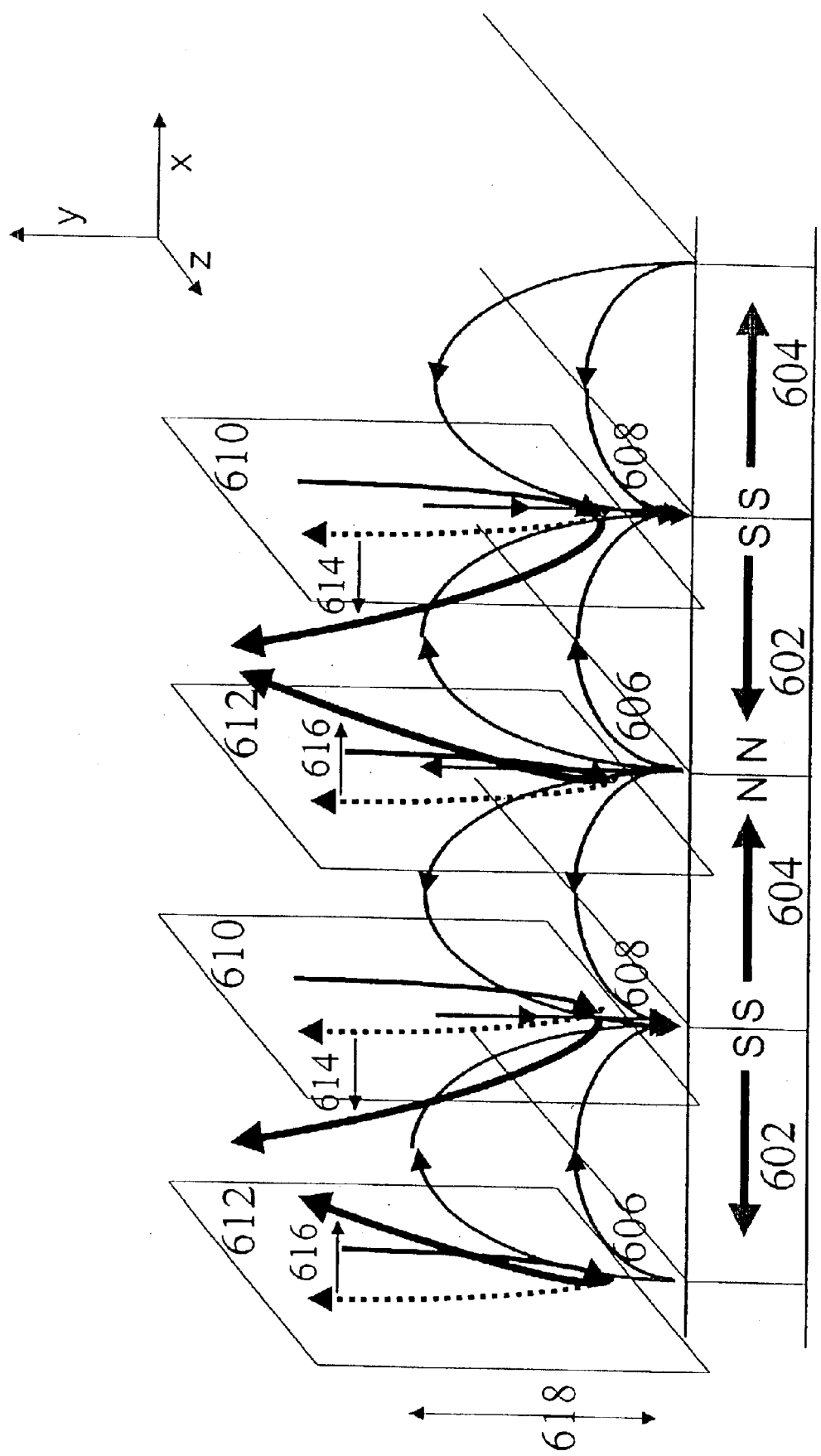
FIG. 6 is a schematic illustration depicting electrons from a tilted incident beam in accordance with an embodiment of the invention.

FIG. 6 is a first schematic illustration depicting electrons from a tilted incident beam in accordance with an embodiment of the invention. The electron trajectories 614 and 616 for the tilted beam are illustrated. These electron trajectories 614 and 616 develop a velocity component coming out of the yz plane 610 and 612 and are deflected either to the right or the left.

In this case, in accordance with the Lorentz force equation, applicants believe that the electrons from the tilted beam are substantially influenced by the downwardly flowing 608 or upwardly flowing 606 field lines near the borders between magnetic domains (602 and 604). Specifically, the tilted electrons incident in the yz plane 612 above the downward flowing field lines 608 are deflected towards the right following the trajectory 616. This is due to the Lorentz force acting on the velocity component pushing the electrons to the right in the horizontal x direction. Meanwhile, the tilted electrons incident in the yz plane 610 above the upward flowing field lines 606 are deflected towards the left. Again, this is due to the Lorentz force acting on the velocity component pushing electrons to the left in the horizontal x direction.

As shown in FIG. 6, applicants believe that the Lorentz forces cause the tilted electrons to have trajectories such that the electrons become more concentrated or densely populated above every other domain. In this specific case, the regions 618 above the domains with leftward magnetic direction 604 are more populated with electrons than the regions 618 above the domains with rightward magnetic direction 602.

In accordance with an embodiment of the invention, the focus of the electron inspection apparatus 100 may be set or defocused such that the above-discussed regions 618 are in focus. In addition, the specimen 112 may be biased at a slightly negative voltage with respect to the mirror potential such that the incident electrons slow down as they approach the surface and are primarily reflected in the region 618 that is above the surface. In such a system, applicants believe that high magnetic contrast is achievable, as demonstrated by the first image A in FIG. 2.

Note that the above-described technique should also be usable to inspect magnetic materials where the orientation of the magnetizations is perpendicular rather than longitudinal. In that case, the magnetic field lines would flow upward in the regions above the magnetic bits with upward magnetization direction, and the magnetic field lines would flow downward in the regions above the magnetic bits with downward magnetization direction. The electron trajectories from tilted incident beams would be concentrated in a similar fashion in particular regions above the bits, and high magnetic contrast would again be achievable.

The above-described diagrams are not necessarily to scale and are intended be illustrative and not limiting to a particular implementation. The above-described invention may be used in an automatic inspection or review system and applied to the inspection or review of magnetic recording media, magnetic read/write heads, and similar magnetic structures. In the case of inspecting magnetic media, the high magnetic contrast available with this technique should enable, for example, the imaging of a typical hard disk in about an hour or less. Furthermore, in contrast to the conventional technique of reading the media with a magnetic reader head, the above-discussed technique should also advantageously provide for higher spatial resolution. In the case of inspecting read/write heads, this technique should enable inspection of a full bar of heads. This contrasts with the expensive and time consuming conventional technique of dicing, individually mounting, and individually testing each head. In the future, this technique or a variation thereof may be advantageously used to inspect or review advanced magnetic media wherein the magnetic bits are isolated from each other.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

what is claimed is:

1. A method for inspecting or reviewing a magnetized specimen using an automated inspection apparatus, the method comprising:

generating a beam of incident electrons using an electron source;

biasing the specimen with respect to the electron source such that the incident electrons decelerate as a surface of the specimen is approached;

illuminating a portion of the specimen with the beam of incident electrons at a tilt;

moving the specimen under the beam of incident electrons using a movable stage of the inspection apparatus; and detecting scattered electrons to form image data of the specimen showing distinct contrast between regions of different magnetization.

2. The method of claim 1, wherein the movement of the specimen under the beam of incident electrons is continuous, and wherein the detection of the scattered electrons acquires data for multiple image pixels in parallel and is performed using a time delay integrating detector.

3. The method of claim 1, wherein the specimen is biased such that incident electrons are primarily reflected above a surface of the specimen.

4. The method of claim 1, further comprising:

adjusting a focus of the beam of incident electrons by adjusting a strength of an objective electron lens; and adjusting a tilt of the beam of incident electrons.

5. The method of claim 1, further comprising:

separating the scattered electrons from the beam of incident electrons using a beam separator device;

projecting the scattered electrons onto an image forming device; and impinging a second beam of electrons onto the specimen for controlling surface charge.

6. The method of claim 1, wherein the magnetic specimen comprises a magnetic storage medium.

7. The method of claim 6, further comprising:

extracting binary data from the image data, wherein the binary data represents information stored on the magnetic storage medium.

8. The method of claim 1, wherein the magnetic specimen comprises an array of read/write heads.

9. The method of claim 8, further comprising:

inspection of the read/write heads to detect faulty heads prior to dicing and individual testing of the heads.

10. A method for recovering data from a magnetic storage medium, the method comprising:

generating a beam of incident electrons using an electron source;

biasing the medium with respect to the electron source such that the incident electrons decelerate as a surface of the medium is approached;

illuminating a portion of the medium with the beam of incident electrons at a tilt;

detecting scattered electrons to form image data of the medium showing distinct contrast between magnetic bits; and extracting binary data from the image data.

11. The method of claim 10, further comprising:

decoding the binary data to recover data previously stored on the magnetic storage medium.

12. An automated inspection apparatus configured to inspect arrays of magnetic read/write heads, the apparatus comprising:

an electron source for generating a beam of incident electrons;

a bias circuit for biasing an array of heads with respect to the electron source such that the incident electrons decelerate as a surface of the array of heads is approached;

electron optics for illuminating the array of heads at a tilt with the beam of incident electrons;

a movable stage for moving the array of heads under the beam of incident electrons; and a detector for detecting scattered electrons to form image data of the array of heads showing a high level of magnetic contrast.

13. The apparatus of claim 12, wherein the apparatus is utilized to inspect the array of heads to detect faulty heads prior to dicing and individual testing of the heads.

14. The apparatus of claim 12, wherein the movable stage is moved continuously under the beam of incident electrons, and wherein the detector comprises a parallel detector that acquires data for multiple image pixels in parallel to form the image data.

15. The apparatus of claim 14, wherein the parallel detector comprises a type of time delay integrating detector.

16. The apparatus of claim 12, further comprising:

a deflector which is configured to modify a tilt of the beam of incident electrons; and an objective lens for adjusting a focus of the beam of incident electrons.

17. The apparatus of claim 12, wherein the movable stage is biased such that incident electrons are primarily reflected above a surface of the array of heads.

18. The apparatus of claim 12, further comprising:

a beam separator for separating the scattered electrons from the beam of incident electrons;

a projection lens for projecting the scattered electrons onto an image forming device; and a second electron source for generating a second beam of electrons for use in controlling surface charge.

19. An apparatus configured to examine a magnetic storage medium, the apparatus comprising:

an electron source for generating a beam of incident electrons;

a bias circuit for biasing the medium with respect to the electron source such that the incident electrons decelerate as a surface of the medium is approached;

electron optics for illuminating the medium at a tilt with the beam of incident electrons;

a detector for detecting scattered electrons to form image data of the medium showing distinct magnetic contrast; and an image processor for extracting binary data from the image data.

20. The apparatus of claim 19, further comprising:

a data decoder for decoding the binary data to recover data previously stored on the magnetic storage medium.

21. An automated inspection system for inspecting or reviewing a magnetized specimen, the system comprising:

means for generating a beam of incident electrons using an electron source;

means for biasing the specimen with respect to the electron source such that the incident electrons decelerate as a surface of the specimen is approached;

means for illuminating a portion of the specimen with the beam of incident electrons at a tilt;

means for moving the specimen under the beam of incident electrons using a movable stage of the inspection apparatus; and means for detecting scattered electrons to form image data of the specimen showing distinct contrast between regions of different magnetization.

22. A system for recovering data from a magnetic storage medium, the system comprising:

means for generating a beam of incident electrons using an electron source;

means for biasing the medium with respect to the electron source such that the incident electrons decelerate as a surface of the medium is approached;

means for illuminating a portion of the medium with the beam of incident electrons at a tilt;

means for detecting scattered electrons to form image data of the medium showing distinct contrast between magnetic bits; and means for extracting binary data from the image data.

* * * * *